United States Patent
Kuwabara

[19]

[11] Patent Number: 6,055,875
[45] Date of Patent: May 2, 2000

[54] MEASURING APPARATUS

[75] Inventor: Shoji Kuwabara, Ibaraki, Japan

[73] Assignee: Shimadzu Corporation, Kyoto, Japan

[21] Appl. No.: 09/179,592

[22] Filed: Oct. 27, 1998

[30] Foreign Application Priority Data

Oct. 29, 1997 [JP] Japan ................................. 9-296978
Jun. 10, 1998 [JP] Japan ................................ 10-162023

[51] Int. Cl.$^7$ ................................................. G01N 1/00
[52] U.S. Cl. .......................................................... 73/866
[58] Field of Search .............................. 73/431, 821, 830,
73/834, 848, 851, 866, 863.11, 863.12,
864.23, 864.24, 290 B; 374/45–57; 250/341.1–341.8,
522.1, 491.1, 358.1

[56] References Cited

U.S. PATENT DOCUMENTS

3,535,914 10/1970 Veith et al. .
5,251,497 10/1993 Bressan ................................. 73/856.6
5,281,535 1/1994 Wei et al. ............................... 73/865.6
5,507,193 4/1996 Ishihara .

*Primary Examiner*—Robert Raevis
*Attorney, Agent, or Firm*—Kanesaka & Takeuchi

[57] ABSTRACT

A measuring apparatus is formed of a main body for forming a measuring apparatus, a cover disposed on the main body for covering the same, and a pair of elevating mechanisms disposed on a side portion of the main body opposite to each other. The elevating mechanisms move the cover in a vertical direction while supporting the cover in a horizontal state. Each elevating mechanism may include a male shaft with an external thread vertically disposed along the vertical direction of the cover, a female member with an internal thread engaging the male shaft, and an elevating table for supporting the cover attached to the female member to be moved up and down in accordance with rotation of the male shaft. The cover is supported on the elevating table to be inclined in the front and rear directions. The male shaft is stopped upon detection of the inclination of the cover by a sensor.

4 Claims, 7 Drawing Sheets

MEASURING APPARATUS

BACKGROUND OF THE INVENTION AND RELATED ART STATEMENT

The present invention relates to a measuring apparatus for analyzing a surface state or composition of a specimen, such as a fluorescence X-ray analyzing apparatus, more particularly, a structure for safely and simply opening or closing a cover of the apparatus in case the specimen is set for measuring.

In the conventional measuring apparatuses, there has been an apparatus wherein laser beams, X-rays or the like are irradiated to a specimen in a vacuum condition to detect light or secondary X-rays generated from the specimen so that a surface state or composition of the specimen is analyzed. In such an analyzing apparatus, though not shown, after the specimen is set on a specimen stand disposed in a main frame of the apparatus and is covered with a cover, an interior of the cover is evacuated to become a vacuum condition. Then, the specimen is irradiated with the laser beams.

Therefore, in case a measuring operation is carried out, after the cover is opened, the specimen is set at a predetermined position. In the conventional measuring apparatus, the cover is generally installed such that the cover is opened or closed with respect to the main frame of the apparatus through a hinge mechanism. Thus, after the cover is manually opened by an operator, the specimen is placed at a predetermined position, and the cover is manually closed.

However, in the measuring apparatus wherein the opening and closing operations of the cover are carried out through the hinge mechanism, since the cover is inclined while moving or orbiting along a circular arc from a horizontal state, even if the cover is opened to a maximum extent, it is difficult to obtain an opening space sufficient for setting the specimen on the specimen stand. Especially, in case the height of a specimen is high, it is difficult to set the specimen.

In order to solve such a problem, although it is considered that the hinge mechanism itself is made large to establish a large opening space for the cover, in case such a structure is employed, a wide space allowing the cover to move along the circular arc around the main frame is required, which is contrary to a demand for miniaturizing the measuring apparatus. Also, there has been a demand for automating the opening and closing operations of the cover, but as long as the hinge mechanism is used, such a request has not been realized because complicated structure and control mechanism are required for the automating operation.

In view of the above defects, the present invention has been made, and an object of the invention is to provide a measuring apparatus, wherein a sufficiently wide opening space of a cover can be obtained.

Another object of the invention is to provide a measuring apparatus as stated above, which has a structure for easily automating the opening or closing operation of the cover.

A further object of the invention is to provide a measuring apparatus as stated above, wherein complicated and troublesome processes in manufacture and maintenance thereof are not required.

A still further object of the invention is to provide a measuring apparatus as stated above, wherein a malfunction and damage of the measuring apparatus are prevented while ensuring safety.

Further objects and advantages of the invention will be apparent from the following description of the invention.

SUMMARY OF THE INVENTION

According to a first aspect of the invention, a measuring apparatus includes a pair of elevating mechanisms provided on both sides of a main frame or main body of the apparatus to elevate or lower a cover for the main frame while keeping the cover in a horizontal state.

According to a second aspect of the invention, each elevating mechanism in the measuring apparatus includes a male shaft with an external thread disposed rotatably and arranged vertically in an elevating or lowering direction of the cover; a female member with an internal thread attached to an elevating table for supporting the cover to be elevated or lowered in accordance with rotation of the male shaft; and a guide rod aligned with the male shaft to guide the elevating table vertically.

According to the structure as described above, the cover is elevated or lowered by the elevating mechanisms provided on both sides of the main frame while keeping its horizontal state. Since the cover is elevated or lowered without moving along the circular arc, while an opening space of the cover sufficient for setting a specimen on a specimen stand is established, the measuring apparatus can be made small. Also, since the measuring apparatus has the structure for elevating or lowering the cover corresponding to the rotation of the male shaft, the measuring apparatus of the invention can be automated simpler, at a cheaper cost, than an apparatus where the cover is opened or closed by the hinge mechanism.

In case the elevating mechanisms as described above are employed, although the cover can be opened and closed quickly, since the cover is lowered while keeping its horizontal posture, there may be a risk that a hand of an operator is sandwiched between the cover and the specimen stand if the hand inadvertently remains on the specimen stand. Not only the operator's hand but also a solid substance, such as a set specimen, may be sandwiched between the cover and the specimen stand. In such a case, the cover sandwiching the obstacle together with the specimen stand inclines, by which an unbalanced force is applied to the elevating mechanisms. As a result, the elevating mechanisms may be damaged or do not operate properly.

Further, in order to set a specimen on the specimen stand, it may be preferable to further open the cover opened to a maximum extent, so that a wider opening space is obtained. Therefore, in order to meet such a requirement while preventing the disadvantages as mentioned above, in case an operator's hand or the set specimen is sandwiched between the cover and the specimen stand, it is preferable that the cover is slightly inclined in a front or rear direction to prevent the obstacle. Also, after the cover is inclined to a certain extent, preferably, an opening or closing operation of the cover is stopped to ensure safety and to prevent the elevating mechanisms from malfunctioning or being damaged.

To solve the above problems, there is considered a structure, what is called a "seesaw-like structure", wherein a cover is supported by supporting shafts provided at side positions corresponding to a gravity center of the cover. A third aspect of the invention includes this feature.

In a measuring apparatus according to the third aspect of the invention, the cover is supported by the elevating table to be inclined in the front or rear direction. The apparatus further includes a sensor for detecting an inclination of the cover in the front or rear direction, and a controlling portion for stopping rotation of the male shaft corresponding to the inclination detected by the sensor. In case the structure as described above is employed and the operator's hand or specimen is sandwiched between the cover and the specimen stand, the cover is slightly inclined in the front or rear direction to prevent the obstacle, and after the cover is inclined to a certain extent, the opening or closing operation of the cover is stopped. Therefore, while ensuring safety, the elevating mechanisms are prevented from malfunctioning or being damaged.

In this structure, since a balance between the front and rear of the cover must be held accurately, the production process and maintenance of the measuring apparatus become complicated.

In order to solve this matter, the cover may be held horizontally by an elastic force of a spring provided between the cover and the elevating table. In this structure, the cover becomes heavy, so that when an operator's hand is sandwiched between the cover and the specimen stand, the apparatus may not be stopped immediately. It is not easy to provide a measuring apparatus, wherein a cover is inclined only when a defect takes place while normally keeping the cover in the horizontal state.

A measuring apparatus according to a fourth aspect of the invention has been made to solve this matter. The measuring apparatus includes supporting devices provided between the cover and elevating tables on both sides of the cover to allow the cover to incline in a front or rear direction at positions away from a gravity center of the cover in the front and rear directions. Each supporting device is formed of two supporting shafts disposed in the front and rear sides of the gravity center of the cover, an engaging pin, and a linking lever extending over the supporting shafts and the engaging pin. One of the two supporting shafts, i.e. first supporting shaft, allows a base portion of the linking lever to be fitted to an upright plate provided on a side of an elevating table, and the other supporting shaft, i.e. second supporting shaft, is provided to a side portion of the cover to project therefrom. The second supporting shaft penetrates through a middle portion of the linking lever and is fitted into an elongated hole provided to the upright plate, so that the second supporting shaft is vertically moved therein. The engaging pin is provided on the side portion of the cover to project therefrom and to detachably support a forward edge of the linking lever.

Therefore, in the measuring apparatus having the structure as described above, the cover can be inclined in the front or rear direction while being held in a horizontal state without detecting an accurate position of a gravity center of the cover and adjusting a balance between the front and rear of the cover. Further, troublesome and complicated works are not required in a production process and maintenance thereof, and operations for preventing the obstacle can be positively carried out.

DETAILED DESCRIPTION OF PREFERRED EMBODIMENTS

Hereunder, an embodiment of the invention is described with reference to the drawings.

Figure 1:
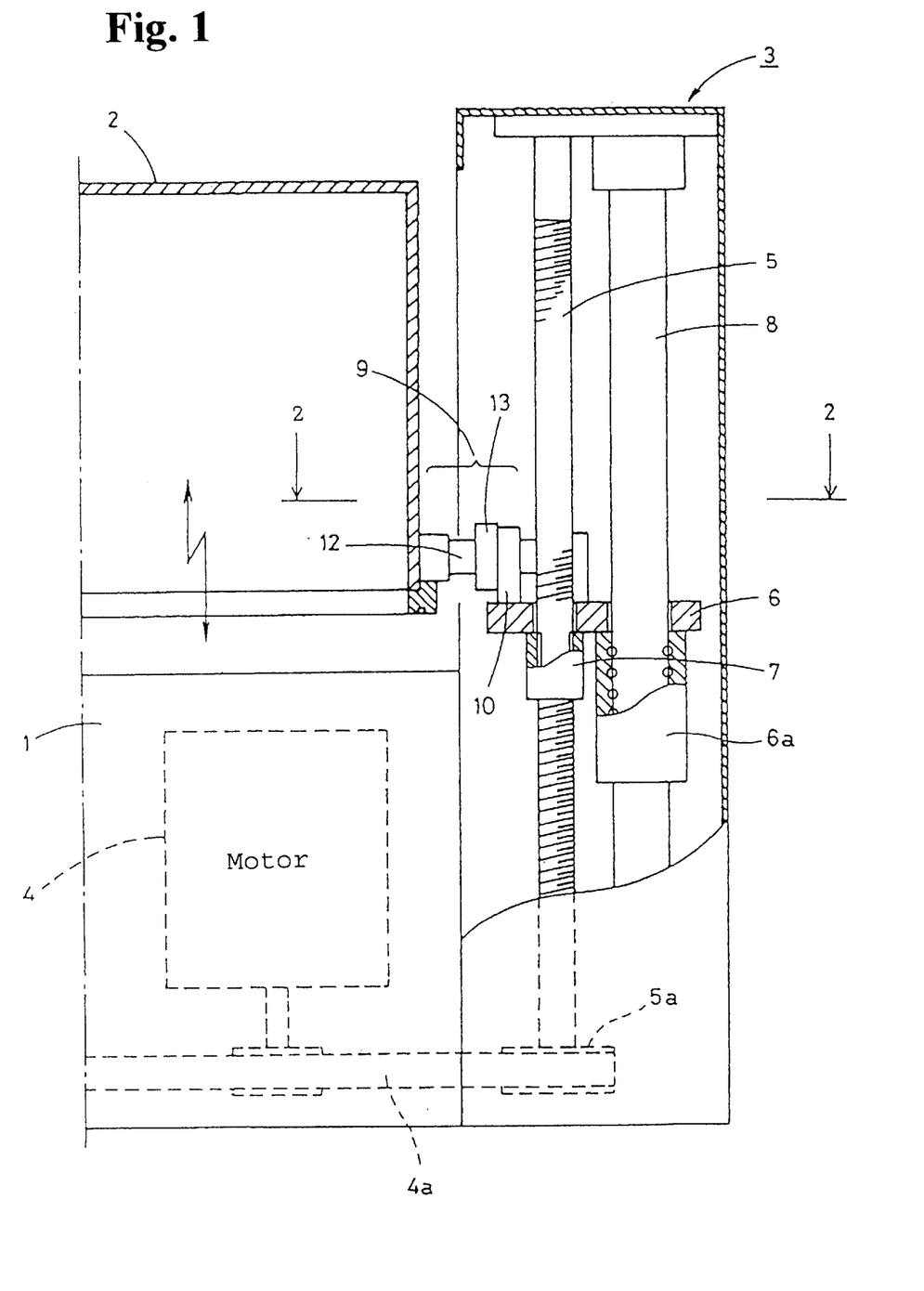
FIG. 1 is a partially sectional front view showing only one side, i.e. right side, of a measuring apparatus of the invention.
Figure 2:
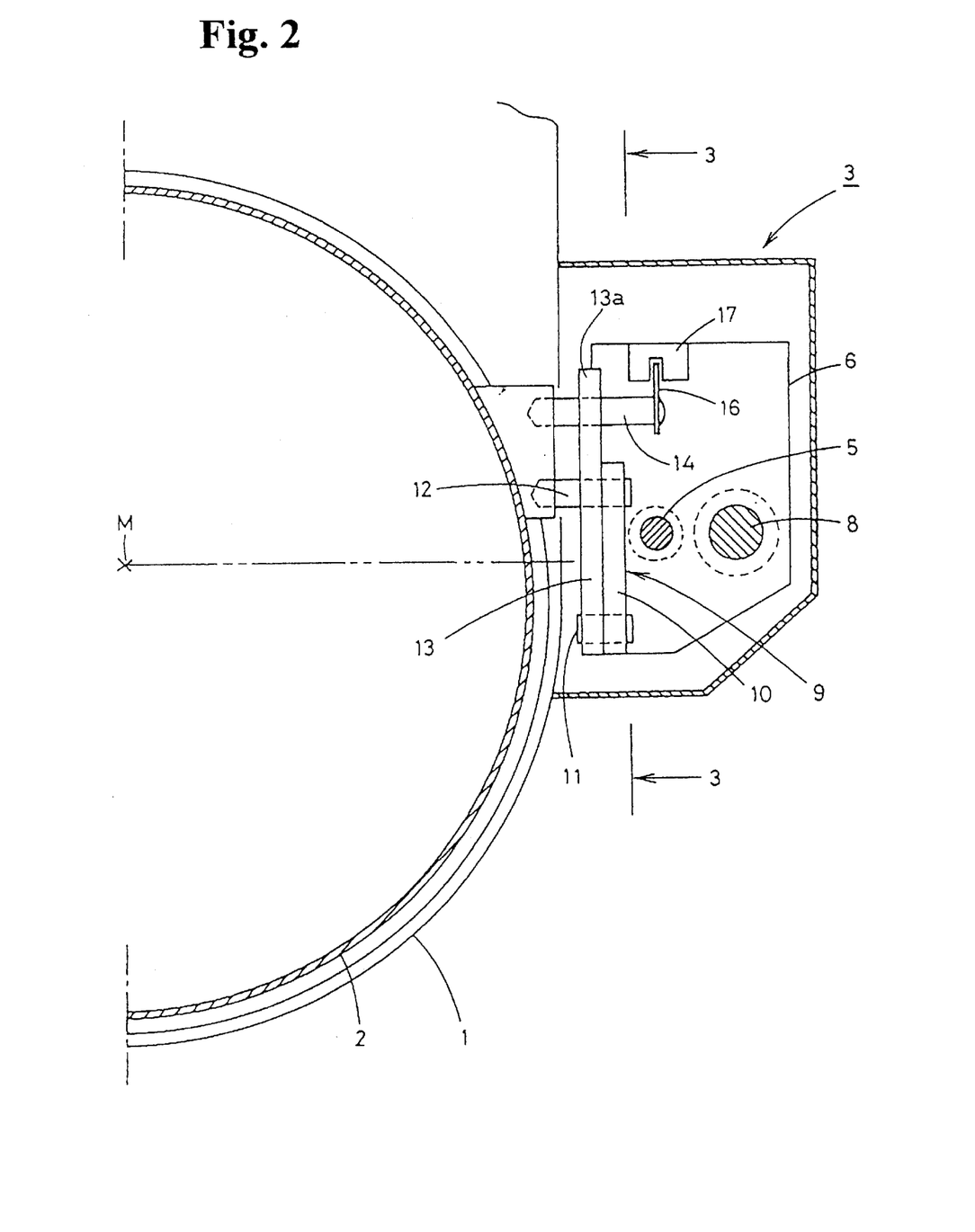
FIG. 2 is a sectional plan view taken along line 2—2 in FIG. 1.
Figure 3:
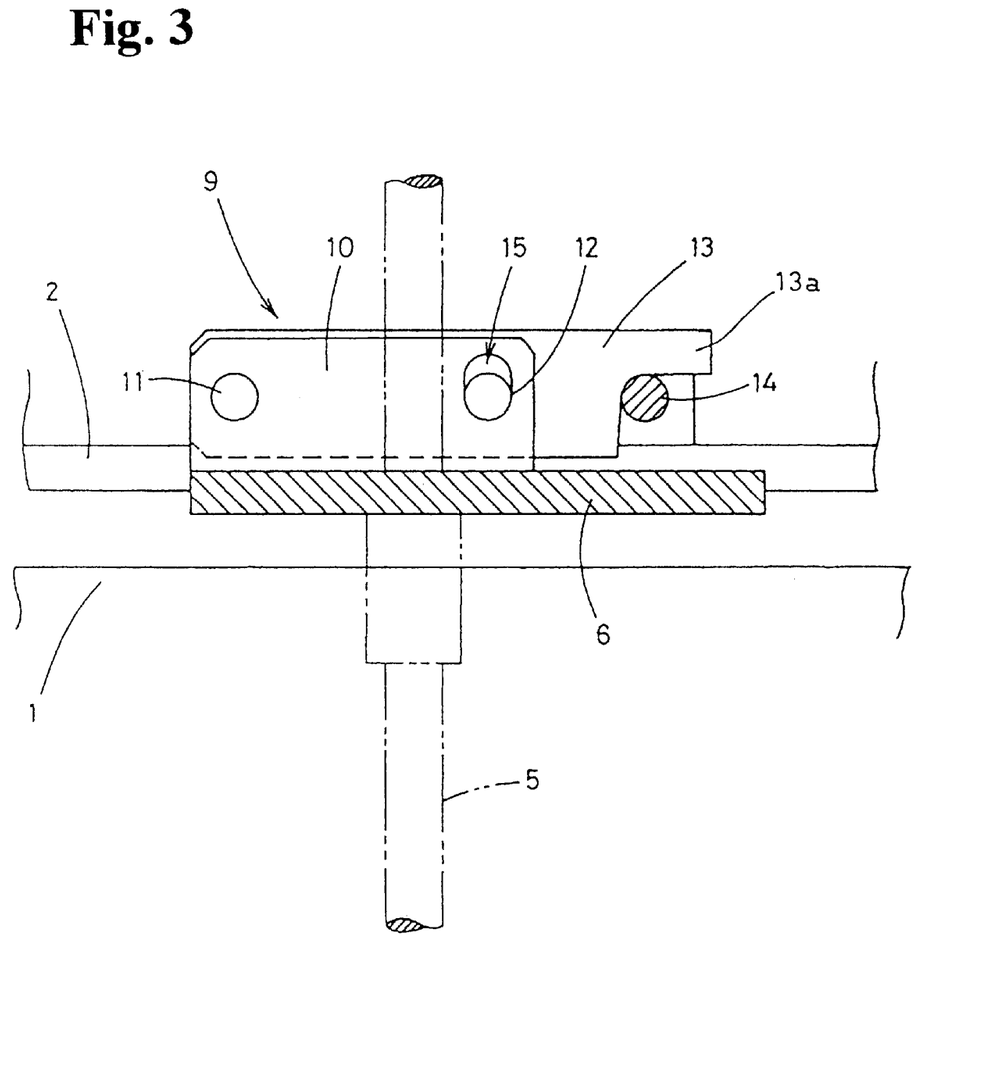
FIG. 3 is an enlarged side view taken along line 3—3 in FIG. 2.
Figure 4:
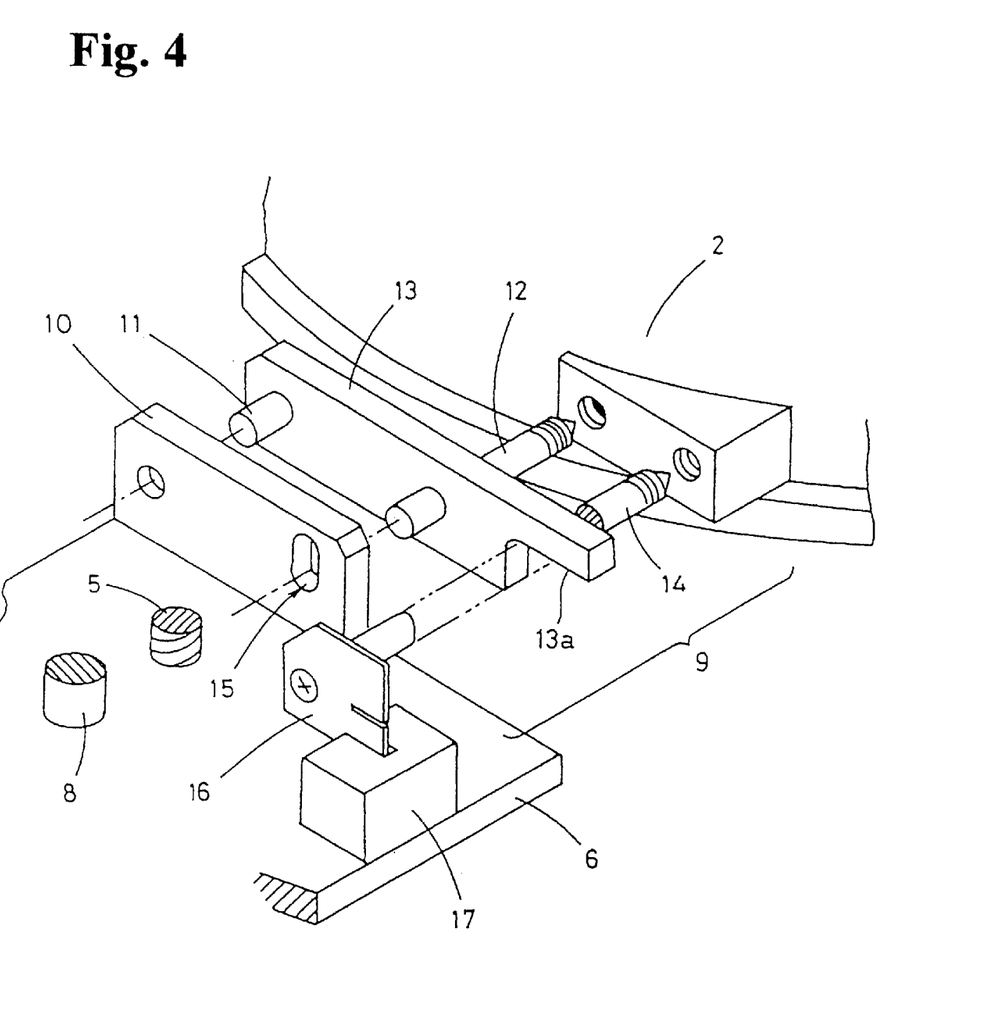
FIG. 4 is an exploded perspective view of the structure shown in FIG. 3.
Figure 5:
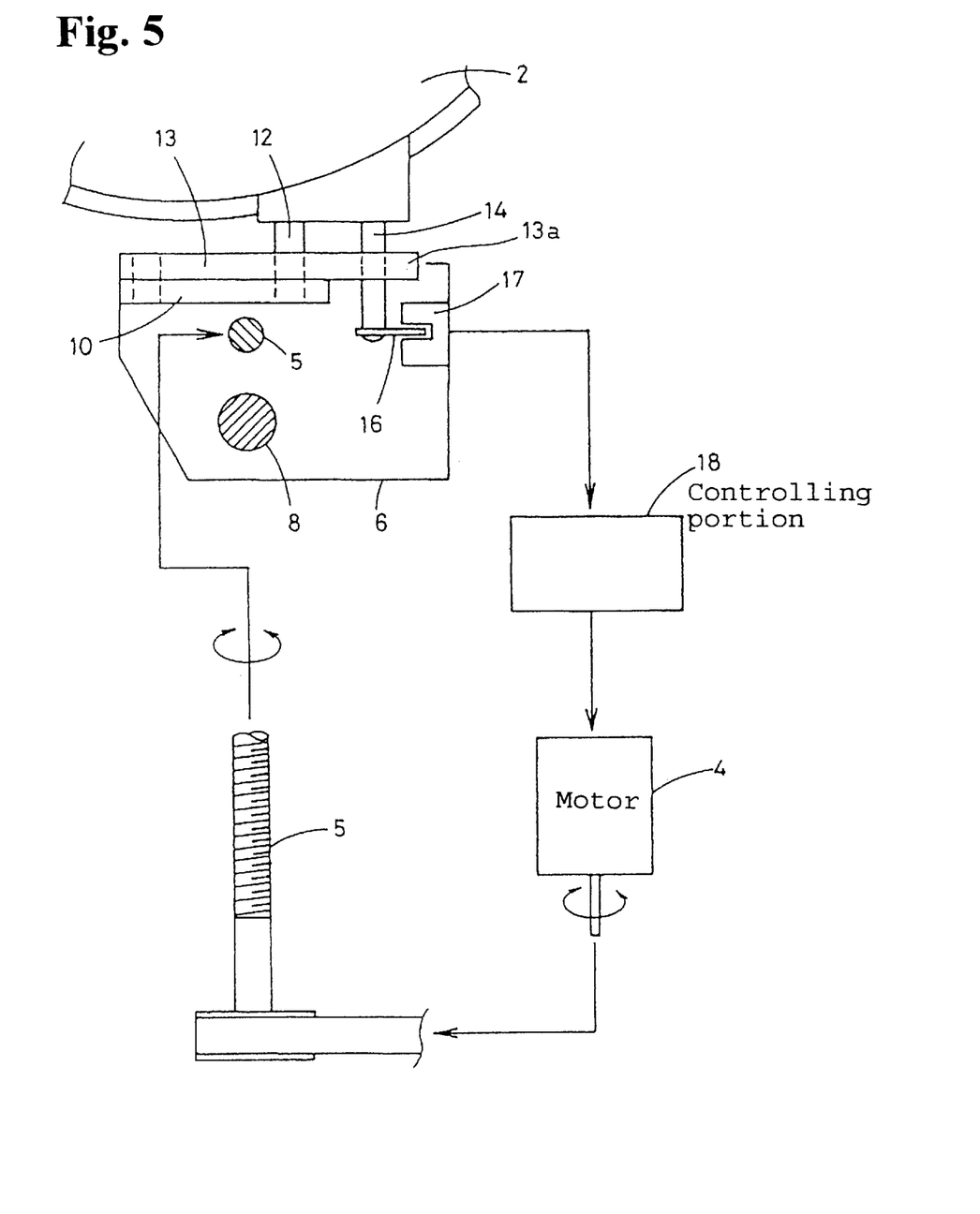
FIG. 5 is an explanatory view showing a circuit structure for controlling movement of an elevating mechanism.

FIGS. 1 to 6 show an essential part of a measuring apparatus of an embodiment of the invention, wherein FIG. 1 is a partially cut front view showing only a right-side portion of the measuring apparatus; FIG. 2 is a sectional plan view taken along line 2—2 in FIG. 1; FIG. 3 is an enlarged side view taken along line 3—3 in FIG. 2; FIG. 4 is an exploded perspective view of the structure as shown in FIG. 3; FIG. 5 is an explanatory view showing a circuit structure for controlling an operation of an elevating mechanism; and FIGS. 6(A) and 6(B) are explanatory views showing movements of a supporting device provided between a cover and an elevating table. Incidentally, FIG. 6(A) shows a state where a forward portion of the cover is elevated, and FIG. 6(B) shows a state where a rear portion of the cover is elevated.

The measuring apparatus of the embodiment according to the invention, as shown in FIG. 1, is formed of a main frame or body 1, and two elevating mechanisms 3 disposed on both sides of the main frame 1 for elevating a cover 2 in a cup shape facing downward while holding the cover in a horizontal state. Each elevating mechanism 3 is vertically disposed in an elevating direction of the cover 2, and includes a male shaft with an external thread, 5 rotated by a motor 4; a female member with an internal thread 7, which is a nut elevated or lowered according to rotation of the male shaft 5 and is attached to an elevating table 6 for supporting the cover 2 through a supporting device 9, described later; and a guide rod 8 aligned with the male shaft 5 to guide an elevating operation of the elevating table 6. The elevating table 6 is guided by the guide rod 8 through a ball bush 6a, i.e. bearing. Incidentally, in FIG. 1, although only the right side elevating mechanism 3 is shown, the same elevating mechanism 3 is provided on the left side of the main frame 1 of the apparatus.

The male shaft 5 for constituting the elevating mechanism 3 is connected to the reversible motor 4 through a belt 4a and a pulley 5a provided at a lower edge thereof. The female member 7 is elevated or lowered according to the rotation of the male shaft 5.

Since the elevating table 6 is elevated or lowered in accordance with the movement of the female member 7, the cover 2 supported by the elevating tables 6 is elevated or lowered while keeping a horizontal state. Incidentally, the respective male shafts 5 located on both sides of the main frame 1 are synchronously rotated since they are connected to the motor 4 through the belts 4a.

Also, at portions corresponding to a maximum opening position and a closing position of the cover 2, there are provided position detecting sensors, such as limit switches (not shown), which are actuated by a dog or the like provided to the respective elevating tables 6. When these position detecting sensors are actuated, rotation of the motor 4 is stopped by a micro-computer, so that the elevating or lowering operation of the cover 2 is stopped.

Further, in the embodiment of the invention, each supporting device 9 formed of supporting shafts, a linking lever and the like is provided between the elevating table 6 and the cover 2, so that the cover 2 elevated or lowered while keeping its horizontal state is inclined in the front or rear direction between the two elevating tables 6 provided on both sides of the cover 2. The supporting devices 9 support the cover 2 at portions away from a gravity center M, as shown in FIG. 2, of the cover 2 in the front or rear direction so that the cover 2 can be inclined in the front or rear direction.

The detailed structure of the supporting device 9 is shown in FIGS. 2 through 4. Each supporting device 9 includes an upright plate 10 integrally provided, in an upright state, to the elevating table 6; two front and rear supporting shafts, i.e. an edge supporting shaft 11 and a penetration supporting shaft 12; a linking lever 13; and an engaging pin 14. The linking lever 13 extends over the supporting shafts 11, 12 and the engaging pin 14.

The edge supporting shaft 11 in the front and rear supporting shafts is located in a front side of the gravity center M of the cover 2, i.e. on a lower side in FIG. 2, such that while allowing the linking lever 13 to swing vertically, a base portion of the linking lever 13 is fitted to the upright plate 10. Also, the other supporting shaft, i.e. the supporting shaft 12, is positioned in a rear side of the gravity center M of the cover 2, i.e. on an upper side in FIG. 2, and projects from a side portion of the cover 2 to the side of the upright plate 10 while passing through a middle part of the linking lever 13. Further, the upright plate 10 has an elongated hole 15 extending in a vertical direction at a position corresponding to the projecting portion of the supporting shaft 12, as shown in FIGS. 3 and 4, so that the projecting portion is fitted therein. Thus, the supporting shaft 12 and the middle part of the linking lever 13 through which the supporting shaft 12 passes are displaced for a length of the elongated hole 15 in the vertical direction.

On the other hand, the linking lever 13 extends rearwardly beyond the supporting shaft 12 to the engaging pin 14. Also, the engaging pin 14 projects from the side portion of the cover 2 to a position corresponding to an extended forward edge 13a of the linking lever 13 to thereby detachably support a lower edge of the extended forward edge 13a of the linking lever 13. Further, as shown in FIGS. 4 and 5, a slit plate 16, as a member to be detected, for detecting an inclination in the front or rear direction of the cover 2 is provided at a, front end of the engaging pin 14. Furthermore, the elevating table 6 is provided with a photosensor 17 for detecting the inclination in the front or rear direction of the cover 2 through the slit plate 16. From these members, a controlling system is constituted. A reference numeral 18 in FIG. 5 denotes a controlling portion formed of a microcomputer, and a signal detected at the photosensor 17 is inputted to the controlling portion 18 so that a stop signal is outputted to the motor 4 for rotating the male shaft 5 corresponding to the detected signal.

Next, an operation of the measuring apparatus having the structure as described above is explained hereunder. First, according to a positive rotation of the motor 4, the male shafts 5 make positive rotations to lift the elevating tables 6. The cover 2 is lifted together by the elevating tables 6, and a specimen stand in the main frame 1 is opened. Then, a specimen is set on a predetermined position of the specimen stand by an operator. Since the cover 2 and the elevating table 6 are connected through the supporting device 9 as described above, the cover 2 opened to a maximum extent can be further pushed upward to incline for placing the specimen on the specimen stand. At this time, since the rotations of the male shafts 5 are stopped, there is no security problems.

Subsequently, after the specimen is set and when the male shafts 5 are reversely rotated, the cover 2 starts to lower down to cover the specimen. During the operation, in case any obstacle does not exist under the cover 2, the cover 2 is lowered while keeping a horizontal state, and the supporting device 9 carries out the following operation. That is, a load of the cover 2 itself is applied to the elevating table 6 through the supporting shaft 12, and as shown in FIG. 3, since the edge portion of the supporting shaft 12 is fitted in the elongated hole 15 of the upright plate 10, the supporting shaft 12 is lowered to the lowermost position to be located at a lower edge of the elongated hole 15. In other words, at this time, the supporting shaft 12 is located at the lowermost position and the middle portion of the linking lever 13 through which the supporting shaft 12 passes is also located at the lowermost position. Thus, the linking lever 13 is kept horizontal as a whole.

In this case, since the gravity center of the cover 2 is located in the front side of the supporting shaft 12, i.e. on the left side in FIG. 3, although the cover 2 is going to incline forward around the supporting shaft 12 as a center, the cover 2 as a whole does not incline forward to keep the horizontal posture because the engaging pin 14 attached to the cover 2 at the rear portion relative to the supporting shaft 12 is supported by the extended forward edge 13a of the linking lever 13. Incidentally, a force for causing the cover 2 to incline forward is applied to the upright plate 10 through the engaging pin 14, linking lever 13 and edge supporting shaft 11, and the load of the cover 2 is shared by the supporting shaft 12 and the edge supporting shaft 11 located in the front and rear sides of the gravity center, which is then supported by a side of the elevating table 6.

Figure 6A:
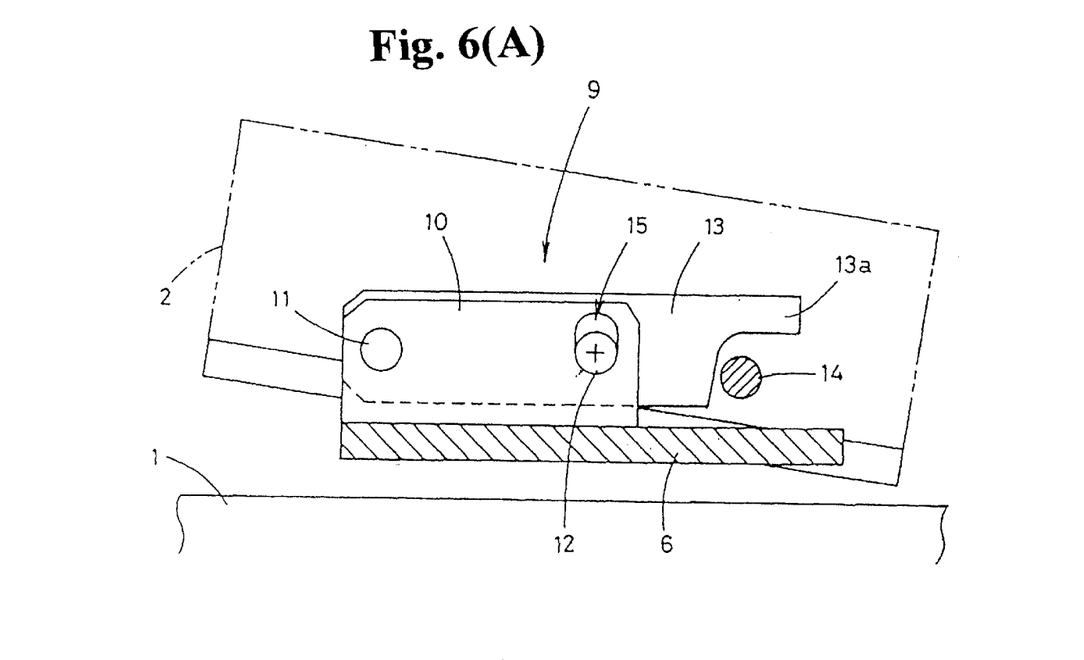
FIGS. 6(A) and 6(B) are explanatory views showing movements of a supporting device provided between a cover and an elevating table.

On the other hand, in case a hand of an operator or specimen is put under a front portion of the lowering cover 2, an external force in a direction to lift the front portion of the cover 2 acts on the cover 2. In this case, the middle part of the linking lever 13 is pressed against the lowermost position of the elongated hole 15 by the supporting shaft 12, as shown in FIG. 6(A), and the base portion of the linking lever 13 is fitted to the upright plate 10. Thus, the cover 2 can not swing in a direction to lift the front portion thereof together with the linking lever 13. On the contrary, in view of the cover 2, the supporting shaft 12 projecting from the cover 2 simply passes through the middle portion of the linking lever 13, so that the supporting shaft 12 can be freely rotated with respect to the linking lever 13. Also, the engaging pin 14 can be moved in a direction away from the extended forward edge 13a of the linking lever 13 in the rear portion of the cover 2. Therefore, the cover 2 at this time is inclined rearward, i.e. in a direction to lift the front portion of the cover 2 around the supporting shaft 12, while keeping the linking lever 13 in the horizontal state.

In case the front portion of the cover 2 is lifted like this and the engaging pin 14 in the rear portion is lowered, since the slit plate 16 attached to the engaging pin 14 is displaced with respect to the photosensor 17 on the elevating table 6, the inclination of the cover 2 is detected by the photosensor 17. A signal detected at this time is inputted into the controlling portion 18, and a stopping signal corresponding to the detected inclination is outputted from the controlling portion 18. Thus, the rotation of the motor 4 is stopped by the stopping signal. Accordingly, the rotations of the male shafts 5 are stopped, and a lowering motion of the cover 2 is stopped. Therefore, an excessive pressing force is not applied to the obstacle sandwiched between the front portion of the cover 2 and the specimen stand.

Figure 6B:
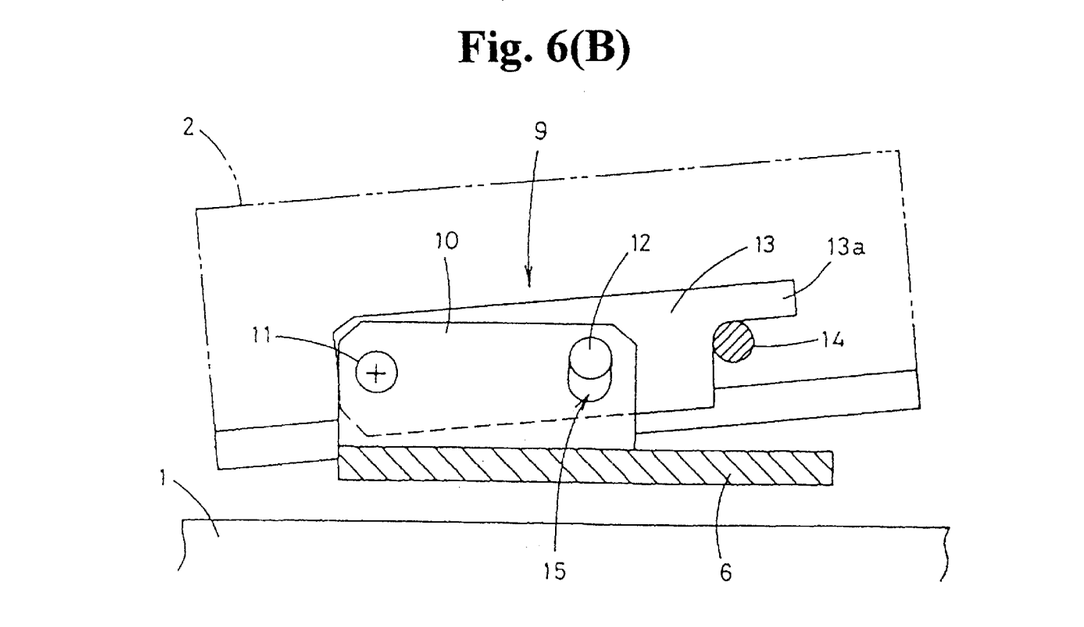

Furthermore, while the cover 2 is lowering, in case an obstacle is put in the rear portion of the cover 2 and an external force in a direction to lift the rear portion of the cover 2 is applied, the cover 2 is apt to incline forward by the external force. In this case, at the rear portion of the cover 2, as shown in FIG. 6(B), since the engaging pin 14 supports the extended forward edge 13a of the linking lever 13, a force in the direction to lift the extended forward edge 13a is applied to the linking lever 13. When such a lifting force is applied, the middle portion of the linking lever 13 is displaced upward for a length of the elongated hole 15 of the upright plate 10, and as a whole, the linking lever 13 swings upward around the edge supporting shaft 11.

However, at this time, since the cover 2 is supported by the linking lever 13 through the supporting shaft 12 and the engaging pin 14, which is united with the linking lever 13, the cover 2 is inclined around the edge supporting shaft 11 together with the linking lever 13. In this case, also, since the engaging pin 14 located at the rear portion of the cover 2 is displaced with respect to the elevating table 6, an inclination of the cover 2 is detected by the photosensor 17. Thus, the rotation of the male shaft 5 is stopped corresponding to the detected inclination thereof, and at the same time, the lowering movement of the cover 2 thereafter is stopped.

Incidentally, in the present embodiment of the invention, although the edge supporting shaft 11 is located in the front portion of the gravity center of the cover 2 and the linking lever 13 is extended rearward, they may be disposed vice versa. In that case, the movements as shown in FIGS. 6(A) and 6(B) are reversed. Also, although the photosensor 17 for detecting the inclination is provided to either one of the elevating tables 6 provided on the left and right sides, sensors like this may be provided at both elevating tables 6. In such a case, the inclination in the right or left direction of the cover 2 can be detected based on a difference between signals detected by the sensors.

Further, the sensor for detecting the inclination of the cover 2 is not limited to the photosensor 17. Since the inclination detecting sensor is provided between a portion which is displaced corresponding to the inclination in the front or rear direction of the cover 2 and a portion which is not inclined, such as the elevating table 6, a proximity switch, micro-switch or the like may be used. Furthermore, the elevating mechanism 3 is not limited to the mechanism formed of the male shaft 5. For example, a mechanism formed of an air cylinder and a magnet valve, or a mechanism formed of a wire moving in a vertical direction may be used.

Incidentally, in the embodiment of the invention, the supporting device 9 including the two supporting shafts 11, 12 and the linking lever 13 is provided between the cover 2 and the elevating table 6, and the cover 2 is supported to be inclined in the front or rear direction at the position apart from the gravity center M of the cover 2 in the front and rear directions. However, in order to prevent a disadvantage when an obstacle is put under a lowering cover 2, in principle, the cover 2 may be supported to be inclined in the front or rear direction. Thus, a supporting mechanism as shown in FIGS. 7 and 8 may be employed.

Figure 7:
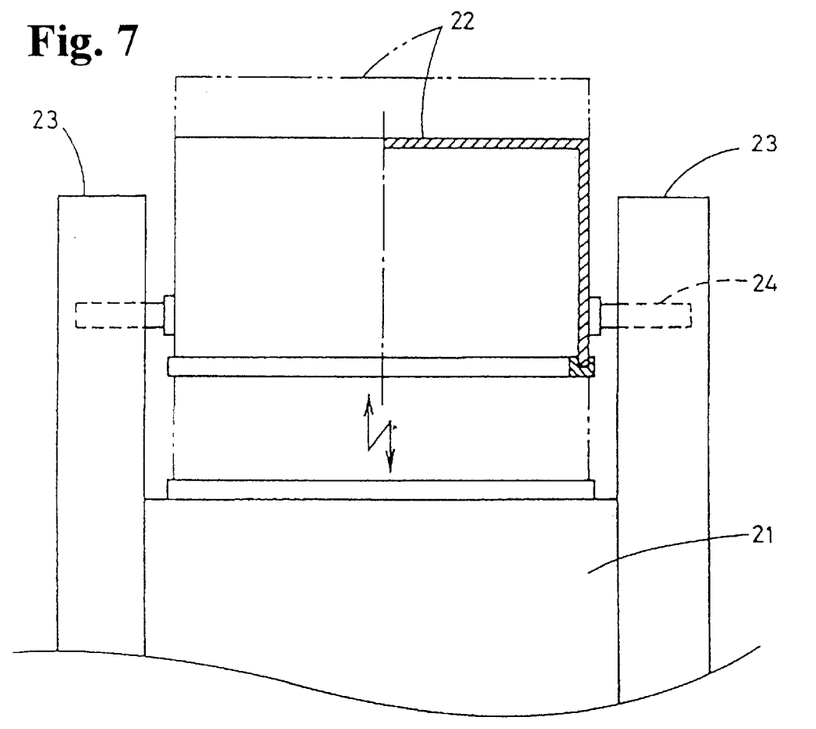
FIG. 7 is an explanatory view showing a structure of the elevating mechanism based on a principle.
Figure 8:
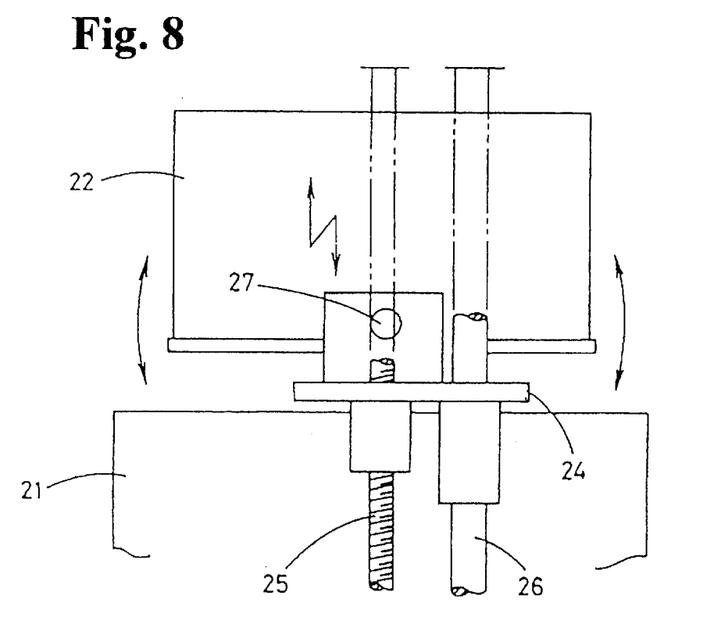
FIG. 8 is an explanatory view showing a structure of the supporting device based on a principle.

As shown in FIG. 7, a cover 22 is elevated or lowered by elevating mechanisms 23 provided on both sides of a main frame 21 of an apparatus while keeping its horizontal state. Incidentally, each elevating mechanism 23 is formed of a male shaft with external thread or simply male shaft, though not shown, and an elevating table 24 elevated or lowered by the male shaft provided between the cover 22 and the male shaft.

In case the elevating mechanisms as described above are employed, although the cover can be opened and closed quickly, since the cover is lowered while keeping its horizontal posture, there may be a risk that a hand of an operator or a solid substance is sandwiched between the cover and the specimen stand. In such a case, when the cover sandwiching the obstacle together with the specimen stand is inclined, an unnatural force is applied to the elevating mechanisms, which results in malfunction or damage of the elevating mechanisms.

Further, it is preferable that the cover opened to a maximum extent in order to set a specimen on the specimen stand may be further pushed upward so that a wider opening space can be obtained.

To solve the above problems, there is considered a structure, what is called a "seesaw-like structure", wherein a cover is supported by supporting shafts provided at side positions corresponding to a gravity center of the cover. An example thereof is shown in FIG. 8, wherein reference numeral 25 designates a male shaft with an external thread for constituting an elevating mechanism, and an elevating table 24 is elevated or lowered through rotation of the male shaft 25. Also, reference numeral 26 is a guide rod for the elevating table 24. The cover 22 at this time is supported by the elevating table 24 through a supporting shaft 27 projecting at both side positions corresponding to the gravity center of the cover 22.

The apparatus further includes a sensor (not shown) for detecting an inclination of the cover in the front or rear direction, and a controlling portion (not shown) for stopping rotation of the male shaft corresponding to the inclination detected by the sensor, similar to the embodiment as shown in FIG. 5. In case the operator's hand or specimen is sandwiched between the cover and the specimen stand, the cover is slightly inclined in the front or rear direction to prevent the obstacle, and after the cover is inclined to a certain extent, the opening or closing operation of the cover is stopped. Therefore, while ensuring safety, the elevating mechanisms are prevented from malfunctioning or being damaged.

However, in case the structure as shown in FIG. 8 is simply employed, after the gravity center of the cover 22 is detected, supporting shafts 27 should be provided to the side positions of the gravity center. Therefore, if setting of the supporting shafts 27 is wrong, the cover 22 is automatically inclined in the front or rear side, so that the cover 22 can not be held horizontally. In this case, the cover 22 can be held horizontally by an elastic force of a spring provided between the cover 22 and the elevating table 24.

According to the measuring apparatus of the invention, since the cover is not moved along a circular arc, the measuring apparatus can be miniaturized while keeping an opening space sufficient for setting the specimen on the specimen stand. Also, as the measuring apparatus is structured so that the cover is elevated or lowered corresponding to a rotation of the male shaft, which is a simpler and cheaper structure and is controlled more easily than that where a cover is automatically opened or closed by a hinge mechanism, an automation thereof can be easily made. Further, in case a hand of an operator or a specimen is put between the cover and the specimen stand, the cover is slightly inclined in the front or rear direction to avoid the obstacle, and an opening or closing operation after the cover is inclined to a certain extent is stopped. Therefore, in the measuring apparatus of the invention, a malfunction or damage of the elevating mechanism can be prevented while ensuring safety.

Further, the present invention meets a request that, in order to set the specimen on the specimen stand, the cover is further moved upward to widely open the inlet even after the cover is opened to a maximum extent. Furthermore, since it is not necessary to detect an accurate gravity center of the cover and to control a balance between the front and rear of the cover, complicated and troublesome procedures in manufacturing the apparatus and its maintenance are not required.

While the invention has been explained with reference to the specific embodiments of the invention, the explanation is illustrative and the invention is limited only by the appended claims.

What is claimed is:

1. A measuring apparatus comprising, a main body for forming a measuring apparatus;

a cover disposed on the main body for covering the same;

a pair of elevating mechanisms disposed on a side portion of the main body opposite to each other, said elevating mechanisms moving the cover in a vertical direction while supporting the cover in a horizontal state, each of said elevating mechanisms including a male shaft with an external thread vertically disposed along the vertical direction of the cover, a female member with an internal thread engaging the male shaft, and an elevating table for supporting the cover attached to the female member to be moved up and down in accordance with rotation of the male shaft, said cover being supported on the elevating table to be inclined in front and rear directions;

a sensor for detecting an inclination of the cover; and a controlling portion connected to the sensor for stopping rotation of the male shaft upon detection of the inclination of the cover by the sensor.

2. A measuring apparatus according to claim 1, wherein each of the elevating mechanisms further includes a guide rod extending along the male shaft to guide the elevating table.

3. A measuring apparatus according to claim 1, further comprising a pair of supporting devices for supporting the cover to be inclined in the front and rear directions, each supporting device being disposed between the cover and the elevating table at a position away from a gravity center of the cover in the front and rear directions so that when an obstacle is disposed between the cover and the main body, the cover is inclined through the supporting device.

4. A measuring apparatus according to claim 3, wherein each of said supporting devices includes first and second supporting shafts to be spaced apart from each other in the front and rear directions with the gravity center of the cover therebetween, an engaging pin attached to the cover, and a linking lever disposed between the cover and the elevating table, said first supporting shaft rotationally connecting the linking lever to the elevating table, the second supporting shaft projecting from the cover and after passing through a middle part of the linking lever fitting into an elongated hole provided in the elevating table to be moved vertically, and said engaging pin projecting from the cover and supporting a lower side of a forward edge of the linking lever.

* * * * *